US 6,539,781 B1

(12) United States Patent
Crezee

(10) Patent No.: US 6,539,781 B1
(45) Date of Patent: Apr. 1, 2003

(54) METHOD AND DEVICE FOR DETERMINING THE HARDNESS OF PRODUCTS SUCH AS FRUIT

(75) Inventor: Leonardus Paulus Crezee, Snelrewaard (NL)

(73) Assignee: FPS Food Processing Systems, B.V. (NL)

( * ) Notice: Subject to any disclaimer, the term of this patent is extended or adjusted under 35 U.S.C. 154(b) by 0 days.

(21) Appl. No.: 10/048,074
(22) PCT Filed: Jul. 31, 2000
(86) PCT No.: PCT/NL00/00548
§ 371 (c)(1), (2), (4) Date: May 2, 2002
(87) PCT Pub. No.: WO01/09602
PCT Pub. Date: Feb. 8, 2001

(30) Foreign Application Priority Data

Jul. 30, 1999 (EP) .............................. 99202495

(51) Int. Cl.[7] .................................................. G01N 3/48
(52) U.S. Cl. ............................................. 73/81; 73/573
(58) Field of Search ........................... 73/81, 573, 586, 73/579, 78, 82

(56) References Cited

U.S. PATENT DOCUMENTS

| 5,152,401 A | * | 10/1992 | Affeldt, Jr. et al. ......... 209/556 |
| 5,691,473 A | * | 11/1997 | Peleg ............................. 73/573 |
| 5,696,325 A | * | 12/1997 | Coucke et al. ................. 73/595 |
| 5,811,680 A | * | 9/1998 | Galili et al. .................... 73/579 |

FOREIGN PATENT DOCUMENTS

| EP | 1238582 A2 | * | 9/2002 | .......... A01K/43/00 |
| GB | WO98/52037 | * | 11/1998 | .......... G01N/33/02 |

* cited by examiner

Primary Examiner—Daniel S. Larkin
Assistant Examiner—Charles Garber
(74) Attorney, Agent, or Firm—Larson & Taylor, PLC

(57) ABSTRACT

In a method for determining the hardness of a product, for instance fruit, during a measuring cycle, comprising: supporting the product, tapping the product with a tapping device at least one position of the product, as a result of which the product as a whole is set in its natural vibration and produces vibration signals, sensing the vibration signals with a signal sensor, and processing the vibration signals with a signal processing device, in which the hardness FRi of the product is determined, and further comprising: sensing the signals produced by the tapping device with a second signal sensor, processing the vibration signals with a second signal processing device, the elastic properties of the product being determined in a volume range around the above at least one position, determining the hardness FIi of the product, comparing FIi and FRi and checking the comparison with a pre-adjusted value, the tapping and sensing with the second signal sensor being repeated when the comparison does not satisfy the pre-adjusted value, the hardness can be advantageously determined, in particular intended for labeling products when selecting and subsequently sorting fruit. A device for carrying out this method can be used both for desk-top applications and for on-line determinations on sorting machines.

10 Claims, 2 Drawing Sheets

METHOD AND DEVICE FOR DETERMINING THE HARDNESS OF PRODUCTS SUCH AS FRUIT

Figure 1:
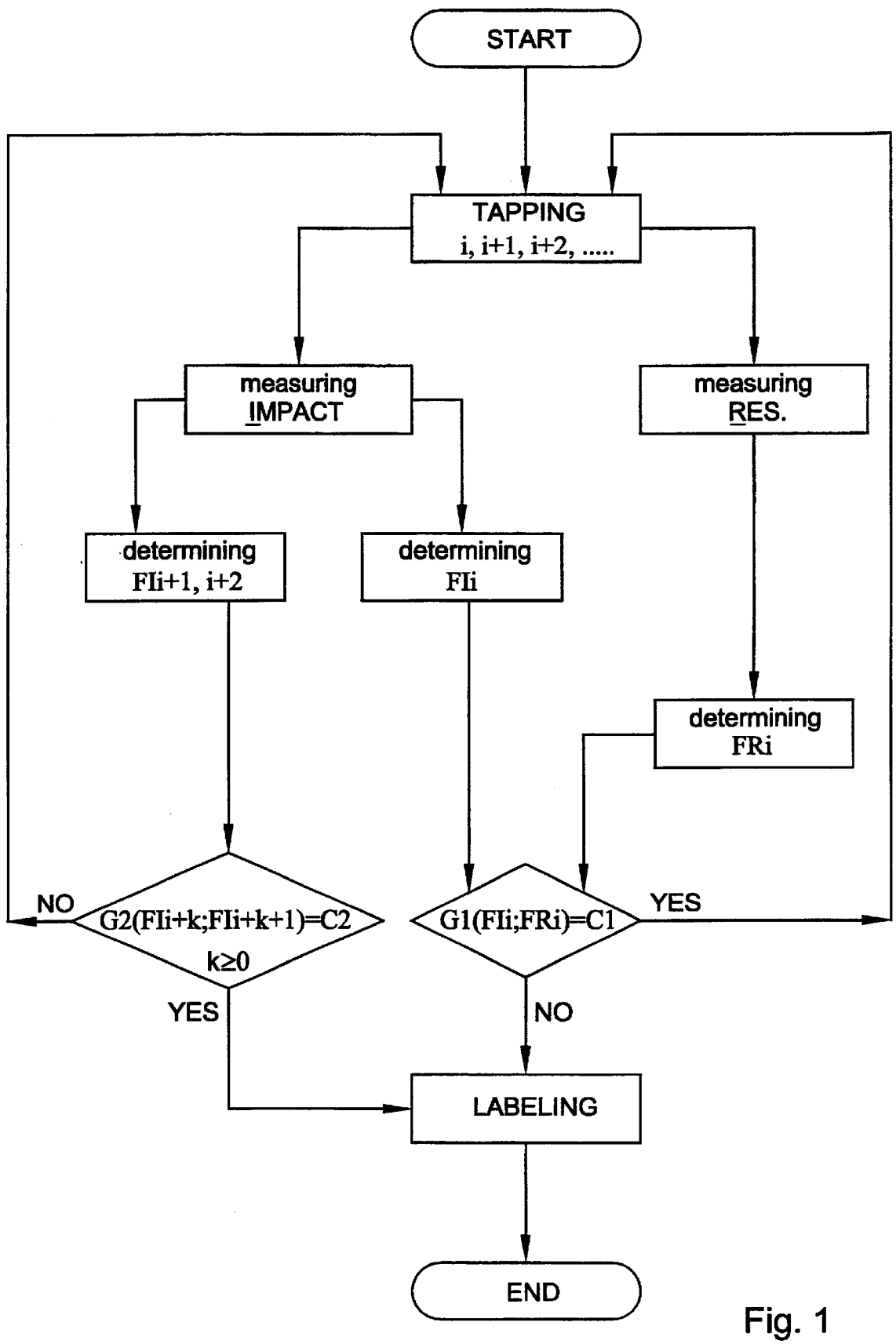

The present invention relates to a method and a device for determining the hardness of products such as fruit. More in particular, the invention relates to a method for determining the hardness of a product, for instance fruit, during a measuring cycle, comprising:
supporting the product,
tapping the product with a tapping device at at least one position of the product, as a result of which the product as a whole is set in its natural vibration and produces vibration signals,
sensing the vibration signals with a signal sensor, and
processing the vibration signals with a signal processing device, in which the hardness FRi of the product is determined, and also to a device for carrying out such a method.

It is known that the tapping of relatively hard products, for instance fruit, but also eggs, causes these products to resonate in one or several of its natural frequencies. The associated signals, in time domain or frequency domain, have been found characteristic of product groups such as apples of a specific variety, eggs, tomatoes, and so on. As soon as such products show damage or other deviations, significant changes occur in the signals.

Such a device is known from U.S. Pat. No. 5,696,325. Eggs lying on rollers of, for instance, a belt conveyor are tapped and thus set in vibration. From the acoustic signals sensed with a signal sensor, such as a microphone, it can be concluded whether the eggs show cracks or fractures. Such devices are used when selecting and sorting eggs.

A survey of such test methods for fruit is given in "New Developments in Fruit Quality Sorting", Itzhak Shmulevich, INTERPOMA 1998, Jun. 4–6, 1998. Tapping of products is referred to therein as "forced vibrations". U.S. Pat. No. 5,811,680 also shows an example thereof, in which the resonance signals caused by tapping of the product are sensed by piezoelectric signal sensors making contact with the product. In the above article the technique in which the hardness is determined via resonance vibrations is referred to, when compared with other techniques, as the most promising.

It has been found that in particular with respect to less hard products, by which the riper products are generally meant, these tapping techniques do not give unambiguous and reproducible results. Tapping on a small overripe spot on an otherwise sound product, or exactly tapping on a stalk, gives a similar drawback. The use of this technique makes selecting and sorting unreliable, or even impossible.

To remove this drawback, the present invention provides a method as indicated above, which is further characterized by
sensing the signals produced by the tapping device with a second signal sensor,
processing the vibration signals with a second signal processing device, the elastic properties of the product being determined in a volume range around the above at least one position.
determining the hardness FIi of the product,
comparing FIi and FRi and checking the comparison with a pre-adjusted value, the tapping and sensing with the second signal sensor being repeated when the comparison does not satisfy the pre-adjusted value.

In this field of the technique such a method is rather known. In the above article it is explained below "detection by impact force" how the course of the tapping or vibration itself, carried out on several spots of the product, also allows the determination of the hardness of such a product. Such a device is described in WO98/52037, in which the reaction force on the tapping element is measured. It is also indicated how such devices can be arranged on a conveyor belt, for instance on both sides of the belt, or also in a wheel rotating above the belt, which configurations allow several times of tapping of the products.

A drawback of such a configuration is not only that for several measurements correspondingly several devices to be mutually calibrated are used, but also that comparison with resonance measurements, and thus feedback, if required, is not possible.

With the device according to the invention the number of measurements can be advantageously limited, which is a necessity in view of the increasing transport and sorting velocities. Moreover, the measuring range is considerably extended with this combination. Sorting machines, or also desk-top arrangements equipped with the device according to the present invention, thus have the great advantage that they are suitable for many kinds of products, and where fruits are concerned, they have the advantage that with respect to a similar type both the hard and the less hard and riper specimen can be compared with each other.

Figure 2:
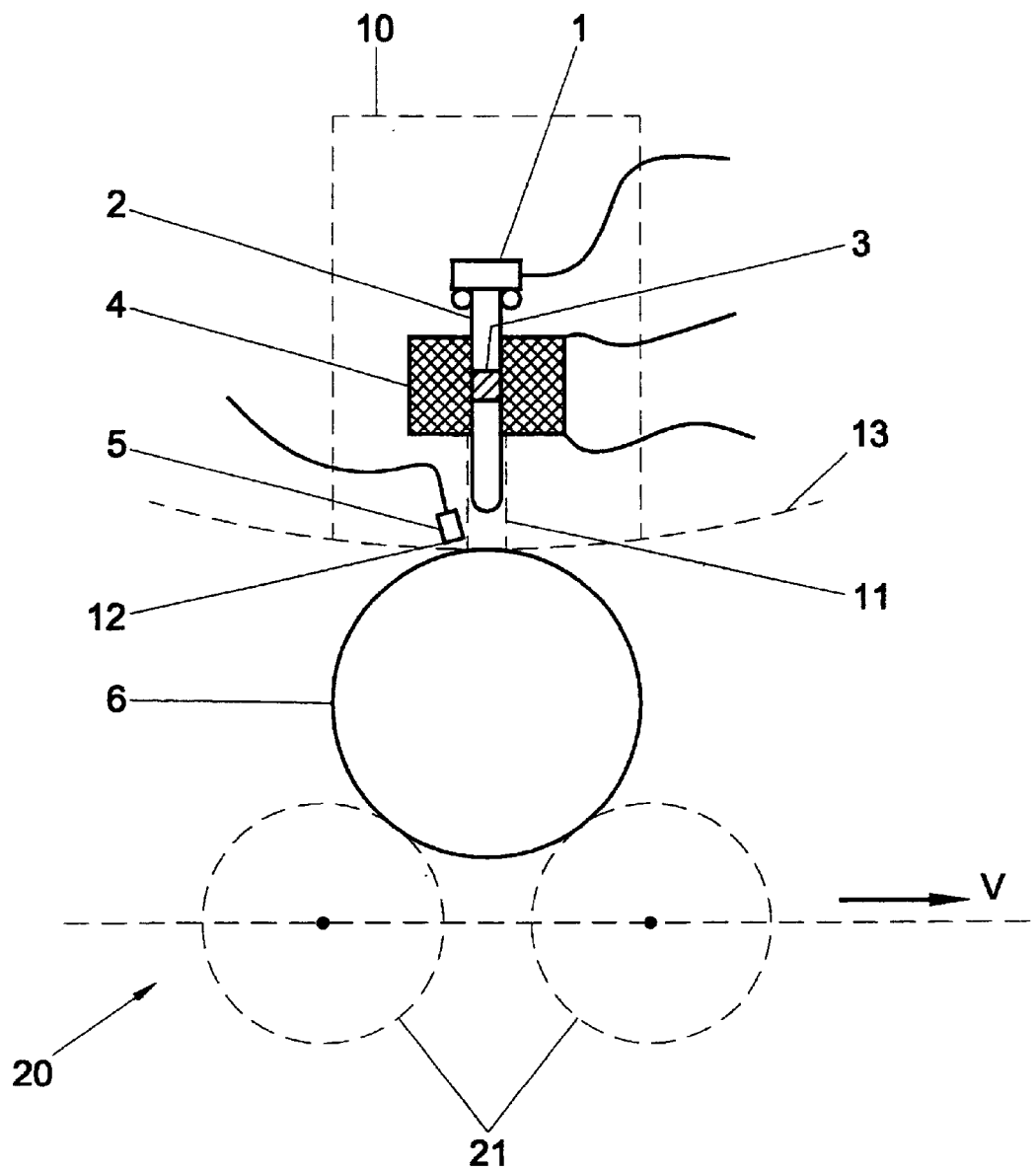

Further details, embodiments and applications will be explained below with reference to some figures in which:

FIG. 1 is a diagram of a practical example of the method according to the invention, and FIG. 2 is a practical example of a tapping device according to the invention.

The flow diagram according to FIG. 1 shows steps for following the method according to the invention. After tapping, two parallel measurements are conducted, on the one hand according to the above-discussed resonance principle, on the other hand according to the impact principle, which latter is to be regarded as the measurement of the reaction of the tap to the tapping device. It will be clear that, although tapping is constantly referred to, this also comprises other methods of setting in vibration. But it will be clear to a skilled worker that setting in vibration generally concerns vibrations of the pulse type. In the above article this is extensively referred to.

After measuring, the hardness is determined according to the relevant measurement in the known manner. In the comparison then to be carried out, both hardness values are compared and checked. This check, in the figure generally designated by a generalized formula G1 with a criterion C1. may comprise, by way of example, a quotient ranging between limit values, a limited resonance value to check the reliability therewith, or a combination of both. It will be clear to every skilled worker that other criteria may be used as well.

When this has been satisfied, the setting in vibration is repeated, and the measurement of the hardness according to the impact principle is repeated. If, on the contrary, the criterion for repetition is not satisfied, then the hardness, which is then assumed to be unambiguous, can be determined, after which the product can be labeled.

In the case of repetition a second hardness value determined according to the principle of hardness will be compared with the preceding value according to a generalized formula G2 with a criterion C2. As mentioned above, this criterion may comprise a quotient between limits, or further similar delimitations and connections. For this criterion, too, it holds that repetition is possible. In the diagram this is indicated for a measuring series i with a corresponding measurement i, and successive measurements i+1, i+2, ..., and generally designated by i+k, i+k+1, ..., k≧0.

The diagram shown in the figure holds for a cycle, carried out on a similar product. For each following product a similar cycle can be carried out, a time span later. This method is suitable both for desk-top arrangements and for on-line measurements on large sorting machines.

By labeling, a new selection criterion can be used for such products in an advantageous and desirable manner. A further advantage is that the measuring range is extended. By this is meant that, since it has been found that the measuring ranges, which, according to each of the vibration principles, know their own limits, connect to each other, practically all the products of a similar kind, for instance both soft and hard tomatoes, can be processed in one and the same selecting and sorting cycle. Accordingly, pre-selection or possible repetition of sorting are superfluous.

Moreover, it will be clear that other diagrams and decision routes can be realized with the combination of these types of measurements, which are comprised by the ideas of combining according to the present invention.

FIG. 2 shows a practical example of a tapping device according to the present invention. A supported product 6, for instance an apple, is brought near a tapping device, for instance built into a housing 10. In particular, the tapping device comprises a coil 4 with a core 2,3 movable therein, in which 3 is made of magnetic material and remains suspended in the coil by its own weight. The other part 2 of the core is made of non-magnetic or magnetizable material, in particular selected in view of weight and tapping properties. The form of the end of the core directed to the product is suitably selected, in general rounded off, and also such that, when tapping, the product is not damaged. Located at the remote end is a second signal sensor 1, for instance an acceleration sensor, which serves for sensing the signals obtained according to the impact principle, for instance a piezo-element with a suitably selected mass thereon, seen at the end. For sensing the resonance signals a first signal sensor 5 is arranged beside the coil, for instance a microphone. Wiring is diagrammatically shown and connects the device in general and the sensors in particular with the control devices and the signal processing devices, for instance a microprocessor as part of a control computer. The first signal sensor 1 may also comprise a number of microphones, for instance arranged in an array. With such a set of microphones an unambiguous resonance signal can be obtained. Moreover, the disadvantageous effect of ambient sound can be removed when measuring is carried out with a number of microphones.

Furthermore, the figure shows an example of a support, for instance rollers 21 of a conveyor belt 20, which moves to the right according to the arrow V. The housing 10 is, for instance, built into a wheel 13 diagrammatically shown, preferably made of generally somewhat resilient material so as to avoid shocks. The wheel will be able to co-rotate over the products rolling on. By suitably connecting the wheel with the sorting machine by means of a lever construction, the tapping device will come down on each of the passing products and will be able to carry out a measuring cycle.

Control and timing are carried out in the known manner. Sensors for launching the core in time, and also for stopping it in time, so as to adapt the tapping velocity, may be comprised, as well as tapping shortly after each other when repetition is necessary.

The housing may also be built into a desk-top arrangement, which enables manual use at unusual locations, such as when harvesting products.

It will be clear to everybody that variants and modifications of the principles explained above are considered to fall within the claims of this application. For instance, positions for the tapping device other than the vertical positions shown are possible.

What is claimed is:

1. A method for determining the hardness of a product, for instance fruit, during a measuring cycle, comprising:
   supporting the product,
   tapping the product with a tapping device at at least one position of the product, as a result of which the product as a whole is set in its natural vibration and produces vibration signals,
   sensing the vibration signals with a signal sensor, and
   processing the vibration signals with a signal processing device, in which the hardness $FRi$ of the product is determined, characterized by
     sensing the signals produced by the tapping device with a second signal sensor,
     processing the vibration signals with a second signal processing device, in which the elastic properties of the product are determined in a volume range around the above at least one position,
     determining the hardness $FIi$ of the product,
     comparing $FIi$ and $FRi$ and checking the comparison with a pre-adjusted value, the tapping and sensing with the second signal sensor being repeated when the comparison does not satisfy the pre-adjusted value.

2. A method according to claim 1, characterized by
   a first comparison G1 for comparing $FIi$ and $FRi$ for a measurement from measuring cycle i,
   checking this comparison with a first criterion C1,
   deciding to repeat tapping when C1 is not satisfied, while in this measuring cycle the measurement i is followed by at least a next i+1 with the second signal sensor, in which in a second comparison G2 for comparing $FIi+k$ and $FRi+1$ with k≧0 a second criterion C2 is checked, and,
   when C2 is not satisfied, a next measurement i+2 with the second signal sensor follows, and
   the hardness being determined, either when terminating the cycle at C1, or when terminating the measuring cycle at C2.

3. A device for determining the hardness of a product, for instance fruit, during a measuring cycle, comprising:
   a support for supporting the product,
   a tapping device for tapping the product at at least one position of the product, as a result of which the product as a whole is set in its natural vibration and produces vibration signals,
   a signal sensor for sensing the vibration signals, and
   a signal processing device for processing the vibration signals, in which the hardness $FRi$ of the product is determined, characterized by
     a second signal sensor for sensing the signals produced by the tapping device,
     a second signal processing device for processing the vibration signals, in which the elastic properties of the product are determined in a volume range around the above at least one position, determining the hardness $FIi$ of the product, and comparing $FIi$ and $FRi$ and checking the comparison with a pre-adjusted value, the tapping and sensing with the second signal sensor being repeated when the comparison does not satisfy the pre-adjusted value.

4. A tapping device according to claim 3, characterized by a housing containing a core movable in an electromagnetic coil, at least part of the core being made of magnetic material, with the tapping end at one end of the core and the second signal sensor at the other end, and with the first signal sensor arranged in the housing beside the coil.

5. A tapping device according to claim 4, characterized by the first signal sensor being a microphone.

6. A tapping device according to claim 4, characterized by the first signal sensor comprising a number of microphones.

7. A tapping device according to claim 4, characterized by the second signal sensor being an acceleration sensor.

8. A tapping device according to claim 3, characterized by the tapping device being built into a wheel which co-rotates with products carried along with a conveyor belt.

9. A tapping device according to claim 8, characterized by the wheel being passed over the fruits with a lever.

10. A tapping device according to claim 3, characterized by the tapping device being built into a desk-top arrangement.

* * * * *

UNITED STATES PATENT AND TRADEMARK OFFICE
CERTIFICATE OF CORRECTION

PATENT NO. : 6,539,781 B1
DATED : April 1, 2003
INVENTOR(S) : Crezee

It is certified that error appears in the above-identified patent and that said Letters Patent is hereby corrected as shown below:

<u>Title page,</u>
Item [*] Notice, change "Notice: Subject to any disclaimer, the term of this patent is extended or adjusted under 35 U.S.C. 154(b) by 0 days" to -- Notice: Subject to any disclaimer, the term of this patent is extended or adjusted under 35 U.S.C. 154 (b) by 429 days --

Signed and Sealed this

Fifth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,539,781 B1
DATED         : April 1, 2003
INVENTOR(S)   : Crezee It is certified that error appears in the above-identified patent and that said Letters Patent is hereby corrected as shown below:

<u>Title page,</u>
Item [*] Notice, change "Notice: Subject to any disclaimer, the term of this patent is extended or adjusted under 35 U.S.C. 154(b) by 429 days" to -- Notice: Subject to any disclaimer, the term of this patent is extended or adjusted under 35 U.S.C. 154(b) by 0 days --

This certificate supersedes Certificate of Correction issued August 5, 2003.

Signed and Sealed this

Twenty-seventh Day of April, 2004

JON W. DUDAS
*Acting Director of the United States Patent and Trademark Office*